(12) United States Patent
Citerone et al.

(10) Patent No.: US 8,835,381 B2
(45) Date of Patent: Sep. 16, 2014

(54) METHODS FOR DETECTING PROTEIN IN PLASMA

(75) Inventors: David Richard Citerone, King of Prussia, PA (US); Charles Scott Hottenstein, King of Prussia, PA (US); Jonathan R. Kehler, King of Prussia, PA (US)

(73) Assignee: Glaxosmithkline LLC, Wilmington, DE (US)

( * ) Notice: Subject to any disclaimer, the term of this patent is extended or adjusted under 35 U.S.C. 154(b) by 798 days.

(21) Appl. No.: 12/663,320

(22) PCT Filed: Jun. 12, 2008

(86) PCT No.: PCT/US2008/066661
§ 371 (c)(1),
(2), (4) Date: Dec. 7, 2009

(87) PCT Pub. No.: WO2008/154619
PCT Pub. Date: Dec. 18, 2008

(65) Prior Publication Data
US 2010/0210470 A1    Aug. 19, 2010

Related U.S. Application Data

(60) Provisional application No. 60/943,383, filed on Jun. 12, 2007.

(51) Int. Cl.
*C07K 14/00* (2006.01)
*G01N 30/02* (2006.01)
*G01N 30/72* (2006.01)
*G01N 33/74* (2006.01)
*G01N 33/68* (2006.01)

(52) U.S. Cl.
CPC ............ *G01N 33/74* (2013.01); *G01N 33/6848* (2013.01)
USPC .................. 514/2; 530/300; 436/88; 436/161

(58) Field of Classification Search
None
See application file for complete search history.

(56) References Cited

U.S. PATENT DOCUMENTS

2006/0141528 A1    6/2006  Aebersold et al.

FOREIGN PATENT DOCUMENTS

| EP | 1 752 770 A1 | 2/2007 |
|---|---|---|
| WO | WO 00/69911 | 11/2000 |
| WO | WO 03/059934 | 7/2003 |
| WO | WO2007/056681 A2 | 5/2007 |

OTHER PUBLICATIONS

Chen et al., "Improving Mass and Liquid Chromatography Based Identification of Proteins Using Bayesian Scoring", Journal of Proteome Research, 4: 2174-2184 (2005).*
Koomen, et al., "Diagnostic protein discovery using liquid chromatography/mass spectrometry for proteolytic peptide targeting", *Rapid Communications in Mass Spectrometry* 19(12):1624-1636 (2005).
Kuhn, et al., "Quantification of C-reactive protein in the serum of patients with rheumatoid arthritis using multiple reaction monitoring mass spectrometry and $^{13}$C-labeled peptide standards", *Proteomics*, 4(4):1175-1186 (2004).
Kehler, et al., "Application of DBS for the quantitative assessment of a protein biologic using on-card digestion LC—MS/MS or immunoassay," *Bioanalysis*, vol. 3, No. 20, pp. 2283-2290 (2011).
Plumb, et al., "Comparison of the quantification of a therapeutic protein using nominal and accurate mass MS/MS," *Bioanalysis*, vol. 4, No. 5, pp. 605-615 (2012).
Szapacs, et al., Absolute quantification of a therapeutic domain antibody using ultra-performance liquid chromatography—mass spectrometry and immunoassay, *Bioanalysis*, vol. 2, No. 9, pp. 1597-1608 (2010).

* cited by examiner

*Primary Examiner* — Anand Desai
(74) *Attorney, Agent, or Firm* — Andrea V. Lockenour; William T. Han (57) ABSTRACT

The present invention provides methods for detecting protein in plasma comprising contacting said plasma with a protease capable of digesting said protein into at least one detectable fragment and detecting said at least one detectable fragment using high performance liquid chromatography and mass spectroscopy.

20 Claims, 4 Drawing Sheets

Figure 1.    Amino Acid Sequence of SEQ ID NO.:1

```
His-Gly-Glu-Gly-Thr-Phe-Thr-Ser-Asp-Val-Ser-Ser-Tyr-Leu-Glu-Gly-Gln-Ala-
Ala-Lys-Glu-Phe-Ile-Ala-Trp-Leu-Val-Lys-Gly-Arg-His-Gly-Glu-Gly-Thr-Phe-
Thr-Ser-Asp-Val-Ser-Ser-Tyr-Leu-Glu-Gly-Gln-Ala-Ala-Lys-Glu-Phe-Ile-Ala-
Trp-Leu-Val-Lys-Gly-Arg-Asp-Ala-His-Lys-Ser-Glu-Val-Ala-His-Arg-Phe-Lys-
Asp-Leu-Gly-Glu-Glu-Asn-Phe-Lys-Ala-Leu-Val-Leu-Ile-Ala-Phe-Ala-Gln-Tyr-
Leu-Gln-Gln-Cys-Pro-Phe-Glu-Asp-His-Val-Lys-Leu-Val-Asn-Glu-Val-Thr-Glu-
Phe-Ala-Lys-Thr-Cys-Val-Ala-Asp-Glu-Ser-Ala-Glu-Asn-Cys-Asp-Lys-Ser-Leu-
His-Thr-Leu-Phe-Gly-Asp-Lys-Leu-Cys-Thr-Val-Ala-Thr-Leu-Arg-Glu-Thr-Tyr-
Gly-Glu-Met-Ala-Asp-Cys-111-111-Cys-Ala-Lys-Gln-Glu-Pro-Glu-Arg-Asn-Glu-
Cys-Phe-Leu-Gln-His-Lys-Asp-Asp-Asn-Pro-Asn-Leu-Pro-Arg-Leu-Val-Arg-Pro-
Glu-Val-Asp-Val-Met-Cys-Thr-Ala-Phe-His-Asp-Asn-Glu-Glu-Thr-Phe-Leu-Lys-
Lys-Tyr-Leu-Tyr-Glu-Ile-Ala-Arg-Arg-His-Pro-Tyr-Phe-Tyr-Ala-Pro-Glu-Leu-
Leu-Phe-Phe-Ala-Lys-Arg-Tyr-Lys-Ala-Ala-Phe-Thr-Glu-Cys-Cys-Gln-Ala-Ala-
Asp-Lys-Ala-Ala-Cys-Leu-Leu-Pro-Lys-Leu-Asp-Glu-Leu-Arg-Asp-Glu-Gly-Lys-
Ala-Ser-Ser-Ala-Lys-Gln-Arg-Leu-Lys-Cys-Ala-Ser-Leu-Gln-Lys-Phe-Gly-Glu-
Arg-Ala-Phe-Lys-Ala-Trp-Ala-Val-Ala-Arg-Leu-Ser-Gln-Arg-Phe-Pro-Lys-Ala-
Glu-Phe-Ala-Glu-Val-Ser-Lys-Leu-Val-Thr-Asp-Leu-Thr-Lys-111-Val-His-Thr-
Glu-Cys-Cys-His-Gly-Asp-Leu-Leu-Glu-Cys-Ala-Asp-Asp-Arg-Ala-Asp-Leu-Ala-
Lys-Tyr-Ile-Cys-Glu-Asn-Gln-Asp-Ser-Ile-Ser-Ser-Lys-Leu-Lys-Glu-Cys-Cys-
Glu-Lys-Pro-Leu-Leu-Glu-Lys-Ser-His-Cys-Ile-Ala-Glu-Val-Glu-Asn-Asp-Glu-
Met-Pro-Ala-Asp-Leu-Pro-Ser-Leu-Ala-Ala-Asp-Phe-Val-Glu-Ser-Lys-Asp-Val-
Cys-Lys-Asn-Tyr-Ala-Glu-Ala-Lys-Asp-Val-Phe-Leu-Gly-Met-Phe-Leu-Tyr-Glu-
Tyr-Ala-Arg-Arg-His-Pro-Asp-Tyr-Ser-Val-Val-Leu-Leu-Leu-Arg-Leu-Ala-Lys-
Thr-Tyr-Glu-Thr-Thr-Leu-Glu-Lys-Cys-Cys-Ala-Ala-Ala-Asp-Pro-His-Glu-Cys-
Tyr-Ala-Lys-Val-Phe-Asp-Glu-Phe-Lys-Pro-Leu-Val-Glu-Glu-Pro-Gln-Asn-Leu-
Ile-Lys-Gln-111-Asn-Cys-Glu-Leu-Phe-Glu-Gln-Leu-Gly-Glu-Tyr-Lys-Phe-Gln-
Asn-Ala-Leu-Leu-Val-Arg-Tyr-Thr-Lys-Lys-Val-Pro-Gln-Val-Ser-Thr-Pro-Thr-
Leu-Val-Glu-Val-Ser-Arg-Asn-Leu-Gly-Lys-Val-Gly-Ser-Lys-Cys-Cys-Lys-His-
Pro-Glu-Ala-Lys-Arg-Met-Pro-Cys-Ala-Glu-Asp-Tyr-Leu-Ser-Val-Val-Leu-Asn-
Gln-Leu-Cys-Val-Leu-His-Glu-222-Lys-Thr-Pro-Val-Ser-Asp-Arg-Val-Thr-Lys-
Cys-Cys-Thr-Glu-Ser-Leu-Val-Asn-Arg-Arg-Pro-Cys-Phe-Ser-Ala-Leu-Glu-Val-
Asp-Glu-Thr-Tyr-Val-Pro-Lys-Glu-Phe-Asn-Ala-Glu-Thr-Phe-Thr-Phe-His-Ala-
Asp-Ile-Cys-Thr-Leu-Ser-Glu-Lys-Glu-Arg-Gln-Ile-Lys-Lys-Gln-Thr-Ala-Leu-
Val-Glu-Leu-Val-Lys-His-Lys-Pro-Lys-Ala-Thr-111-Lys-Glu-Gln-Leu-Lys-Ala-
Val-Met-Asp-Asp-Phe-Ala-Ala-Phe-Val-Glu-Lys-Cys-Cys-Lys-Ala-Asp-Asp-Lys-
Glu-Thr-Cys-Phe-Ala-Glu-Glu-Gly-Lys-Lys-Leu-Val-Ala-Ala-Ser-Gln-Ala-Ala-
Leu-Gly-Leu-  (SEQ ID No.:1)
```

Figure 2:
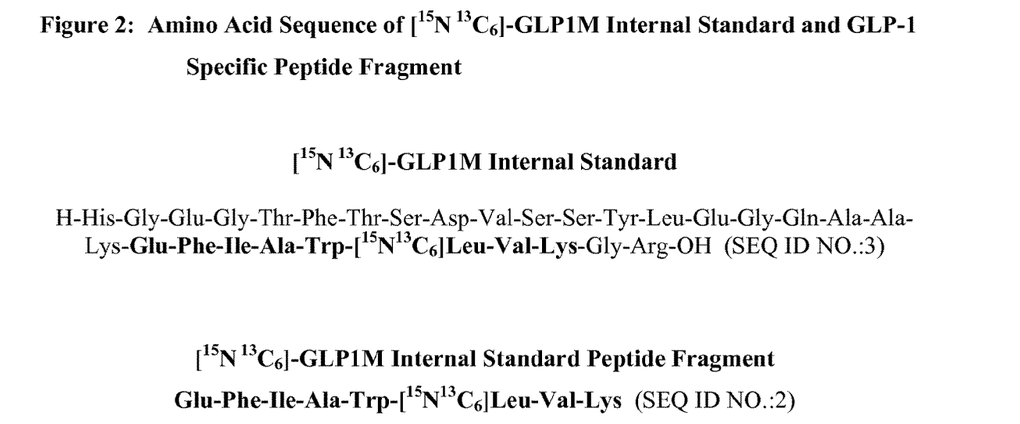

Figure 2: Amino Acid Sequence of [$^{15}$N $^{13}$C$_6$]-GLP1M Internal Standard and GLP-1 Specific Peptide Fragment

[$^{15}$N $^{13}$C$_6$]-GLP1M Internal Standard

H-His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-[$^{15}$N$^{13}$C$_6$]Leu-Val-Lys-Gly-Arg-OH  (SEQ ID NO.:3)

[$^{15}$N $^{13}$C$_6$]-GLP1M Internal Standard Peptide Fragment
Glu-Phe-Ile-Ala-Trp-[$^{15}$N$^{13}$C$_6$]Leu-Val-Lys  (SEQ ID NO.:2)

Figure 3:
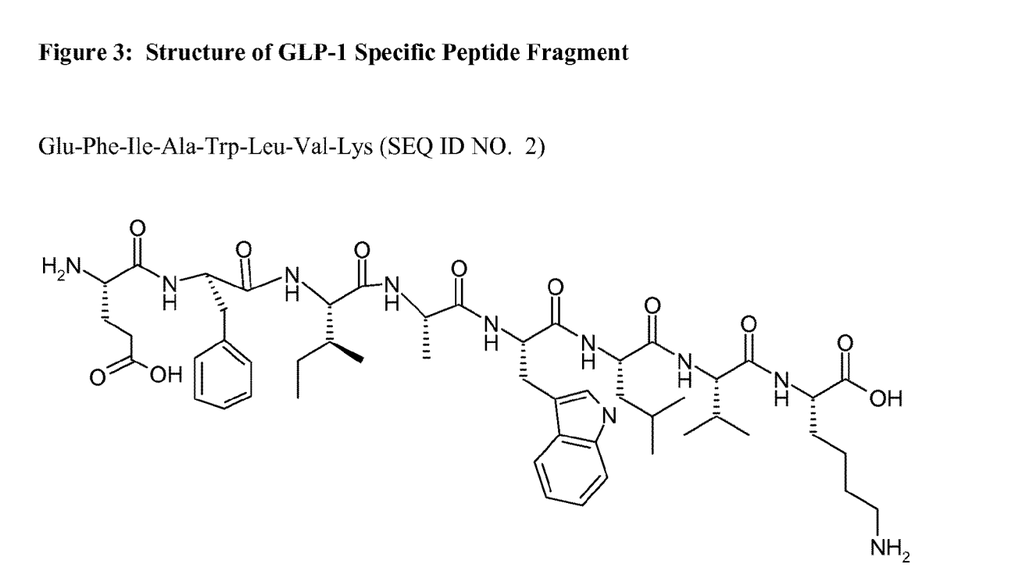

Figure 3: Structure of GLP-1 Specific Peptide Fragment

Glu-Phe-Ile-Ala-Trp-Leu-Val-Lys (SEQ ID NO. 2)

Figure 4:
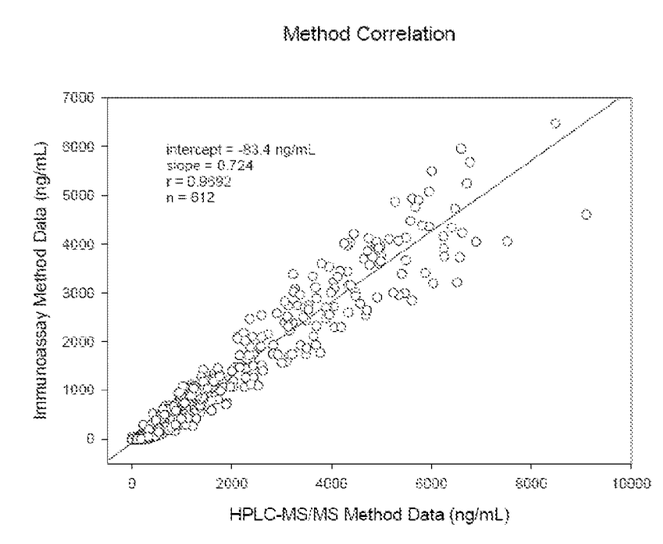

Figure 4: Method correlation plot for data generated using high performance liquid chromatography and mass spectroscopy methods and the ELISA methods.

… ant and/or conjugate thereof. Other hypoglycemic agents include, but are not limited to, drugs that increase insulin secretion (e.g., sulfonylureas (SU) and meglitinides), increase glucose utilization (e.g., glitazones), reduce hepatic glucose production (e.g., metformin), and delay glucose absorption (e.g., α-glucosidase inhibitors).

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques that are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors", *Meth. Enzymol.* (1990) 182:626-646 and Rattan, et al., "Protein Synthesis: Posttranslational Modifications and Aging", *Ann NY Acad Sci* (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

As used herein "fragment," when used in reference to a polypeptide, is a polypeptide having an amino acid sequence that is the same as part but not all of the amino acid sequence of the entire naturally occurring polypeptide. Fragments may be "free-standing" or comprised within a larger polypeptide of which they form a part or region as a single continuous region in a single larger polypeptide. By way of example, a fragment of naturally occurring GLP-1 would include amino acids 7 to 36 of naturally occurring amino acids 1 to 36. Furthermore, fragments of a polypeptide may also be variants of the naturally occurring partial sequence. For instance, a fragment of GLP-1 comprising amino acids 7-30 of naturally occurring GLP-1 may also be a variant having amino acid substitutions within its partial sequence.

As used herein "conjugate" or "conjugated" refers to two molecules that are bound to each other. For example, a first polypeptide may be covalently or non-covalently bounded to a second polypeptide. The first polypeptide may be covalently bound by a chemical linker or may be genetically fused to the second polypeptide, wherein the first and second polypeptide share a common polypeptide backbone.

As used herein "tandemly oriented" refers to two or more polypeptides that are adjacent to one another as part of the same molecule. They may be linked either covalently or non-covalently. Two or more tandemly oriented polypeptides may form part of the same polypeptide backbone. Tandemly oriented polypeptides may have direct or inverted orientation and/or may be separated by other amino acid sequences.

As used herein, "reduce" or "reducing" blood glucose refers to a decrease in the amount of blood glucose observed in the blood of a patient after administration a hypoglycemic agent.

As used herein "diseases associated with elevated blood glucose" include, but are not limited to, Type I and Type II Diabetes and hyperglycemia.

As used herein "co-administration" or "co-administering" as used herein refers to administration of two or more compounds to the same patient. Co-administration of such compounds may be simultaneous or at about the same time (e.g., within the same hour) or it may be within several hours or days of one another. For example, a first compound may be administered once weekly while a second compound is co-administered daily.

"Recombinant expression system(s)" refers to expression systems or portions thereof or polynucleotides of the invention introduced or transformed into a host cell or host cell lysate for the production of the polynucleotides and polypeptides of the invention.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated," as the term is employed herein. Moreover, a polynucleotide or polypeptide that is introduced into an organism by transformation, genetic manipulation or by any other recombinant method is "isolated" even if it is still present in said organism, which organism may be living or non-living.

Intact antibodies include heteromultimeric glycoproteins comprising at least two heavy and two light chains. Aside from IgM, intact antibodies are usually heterotetrameric glycoproteins of approximately 150 Kda, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain (VH) followed by a number of constant regions. Each light chain has a variable domain (VL) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called Framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies. The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade.

A bispecific antibody is an antibody having binding specificities for at least two different epitopes. Methods of making such antibodies are known in the art. Traditionally, the recombinant production of bispecific antibodies is based on the coexpression of two immunoglobulin H chain-L chain pairs, where the two H chains have different binding specificities see Millstein et al, Nature 305 537-539 (1983), WO93/08829 and Traunecker et al EMBO, 10, 1991, 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions, and if desired the L chain are inserted into separate expression vectors and are then cotransfected into a suitable host organism. It is possible though to insert the coding sequences for two or all three chains into one expression vector. A bispecific antibody may be composed of a H chain with a first binding specificity in one arm and a H-L chain pair, providing a second binding specificity in the other arm, see WO94/04690. Also see Suresh et al Methods in Enzymology 121, 210, 1986.

Antibody fragments may be functional antigen binding fragments of intact and/or humanized and/or chimeric antibodies such as Fab, Fab', F(ab')$_2$, Fv, ScFv fragments of the antibodies. Traditionally such fragments are produced by the proteolytic digestion of intact antibodies by e.g. papain digestion (see for example, WO 94/29348) but may be produced directly from recombinantly transformed host cells. For the production of ScFv, see Bird et al. (1988) Science, 242, 423-426. In addition, antibody fragments may be produced using a variety of engineering techniques as described below.

Fv fragments appear to have lower interaction energy of their two chains than Fab fragments. To stabilize the association of the VH and VL domains, they have been linked with peptides (Bird et al, (1988) Science 242, 423-426, Huston et al, PNAS, 85, 5879-5883), disulphide bridges (Glockshuber et al, (1990) Biochemistry, 29, 1362-1367) and "knob in hole" mutations (Zhu et al (1997), Protein Sci., 6, 781-788). ScFv fragments can be produced by methods well known to those skilled in the art see Whitlow et al (1991) Methods companion Methods Enzymol, 2, 97-105 and Huston et al (1993) Int. Rev. Immunol 10, 195-217. ScFv may be produced in bacterial cells such as *E. coli* but are more preferably produced in eukaryotic cells. One disadvantage of ScFv is the monovalency of the product, which precludes an increased avidity due to polyvalent binding, and their short half-life. Attempts to overcome these problems include bivalent (ScFv')$_2$ produced from ScFV containing an additional C terminal cysteine by chemical coupling (Adams et al (1993) Can. Res 53, 4026-4034 and McCartney et al (1995) Protein Eng. 8, 301-314) or by spontaneous site-specific dimerization of ScFv containing an unpaired C terminal cysteine residue (see Kipriyanov et al (1995) Cell. Biophys 26, 187-204). Alternatively, ScFv can be forced to form multimers by shortening the peptide linker to 3 to 12 residues to form "diabodies", see Holliger et al PNAS (1993), 90, 6444-6448. Reducing the linker still further can result in ScFV trimers ("triabodies", see Kortt et al (1997) Protein Eng, 10, 423-433) and tetramers ("tetrabodies", see Le Gall et al (1999) FEBS Lett, 453, 164-168). Construction of bivalent ScFV molecules can also be achieved by genetic fusion with protein dimerizing motifs to form "miniantibodies" (see Pack et al (1992) Biochemistry 31, 1579-1584) and "minibodies" (see Hu et al (1996), Cancer Res. 56, 3055-3061). ScFv-Sc-Fv tandems ((ScFV)2) may also be produced by linking two ScFv units by a third peptide linker, see Kurucz et al (1995) J. Immol. 154, 4576-4582. Bispecific diabodies can be produced through the noncovalent association of two single chain fusion products consisting of VH domain from one antibody connected by a short linker to the VL domain of another antibody, see Kipriyanov et al (1998), Int. J. Can 77, 763-772. The stability of such bispecific diabodies can be enhanced by the introduction of disulphide bridges or "knob in hole" mutations as described supra or by the formation of single chain diabodies (ScDb) wherein two hybrid ScFv fragments are connected through a peptide linker see Kontermann et al (1999) J. Immunol. Methods 226 179-188. Tetravalent bispecific molecules are available by e.g. fusing a ScFv fragment to the CH3 domain of an IgG molecule or to a Fab fragment through the hinge region see Coloma et al (1997) Nature Biotechnol. 15, 159-163. Alternatively, tetravalent bispecific molecules have been created by the fusion of bispecific single chain diabodies (see Alt et al, (1999) FEBS Lett 454, 90-94. Smaller tetravalent bispecific molecules can also be formed by the dimerization of either ScFv-ScFv tandems with a linker containing a helix-loop-helix motif (DiBi miniantibodies, see Muller et al (1998) FEBS Lett 432, 45-49) or a single chain molecule comprising four antibody variable domains (VH and VL) in an orientation preventing intramolecular pairing (tandem diabody, see Kipriyanov et al, (1999) J. Mol. Biol. 293, 41-56). Bispecific F(ab')$_2$ fragments can be created by chemical coupling of Fab' fragments or by heterodimerization through leucine zippers (see Shalaby et al, (1992) J. Exp. Med. 175, 217-225 and Kostelny et al (1992), J. Immunol. 148, 1547-1553). Also available are isolated VH and VL domains (Domantis plc), see U.S. Pat. No. 6,248,516; U.S. Pat. No. 6,291,158; U.S. Pat. No. 6,172,197.

Heteroconjugate antibodies are composed of two covalently joined antibodies formed using any convenient cross-linking methods. See, for example, U.S. Pat. No. 4,676,980.

Hypoglycemic agents may be used in the treatment of both Type I and Type II Diabetes to lower glucose concentration in blood. Insulinotropic peptides have been implicated as possible therapeutic agents for the treatment of diabetes. Insulinotropic peptides include incretin hormones such as, but not limited to, gastric inhibitory peptide (GIP) and glucagon like peptide-1 (GLP-1) as well as fragments, variants, and/or conjugates thereof. Insulinotropic peptides also include exendin 3 and exendin 4. GLP-1 is a 36 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of β-cells. In non-clinical experiments GLP-1 promotes continued beta cell competence by stimulating transcription of genes important for glucose dependent insulin secretion and by promoting beta-cell neogenesis (Meier, et al. *Biodrugs*. 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption.

In people with Type II Diabetes Mellitus, the normal post-prandial rise in GLP-1 is absent or reduced (Vilsboll T, et al., *Diabetes*. 2001. 50; 609-613). Accordingly, the rationale for administering exogenous GLP-1, an incretin hormone, or an incretin mimetic, is to replace or supplement endogenous GLP-1 in order to increase meal-related insulin secretion, reduce glucagon secretion, and slow gastrointestinal motility. Native GLP-1 has a very short serum half-life (<5 minutes). Thus, incretin mimetics used to simulate GLP-1 typically have a longer half-life than endogenous GLP-1.

The present invention provides methods for detecting at least one protein in plasma from a mammal comprising contacting said plasma with a first protease capable of digesting said at least one protein into at least one detectable fragment and detecting said at least one detectable fragment using high performance liquid chromatography and mass spectroscopy.

In one aspect, said at least one protein is a therapeutic protein. In another aspect, said at least one protein is an endogenous protein to said mammal. In yet another aspect, the mammal is a human. Methods of the present invention further comprises calculating pharmacokinetic parameters of at least one therapeutic and/or endogenous protein.

As is understood in the art various methods may be employed to collect, measure and assess pharmacokinetic data such as active compound concentration in blood, plasma and/or other tissue. As is also understood in the art, various methods may be employed to collect, measure and assess various pharmacodynamic data such as, but nor limited to, glucose, insulin, C peptide, glucagons and other biomarker levels in blood and/or plasma and/or other tissue. A skilled artisan will understand the various methods for measuring and calculating the pharmacokinetic (for example, but not limited to, Cmax, AUC, Tmax, serum half-life) and pharmacodynamic (for example, but not limited to, serum, plasma and blood glucose levels) parameters described herein. Furthermore, the skilled artisan will understand the various methods for making statistical comparisons (for example, but not limited to, comparisons of change from baseline to post-treatment and/or comparisons among treatment groups) and/or analysis of the pharmacokinetic and pharmacodynamic parameters described herein. Furthermore, the skilled artisan will understand and be able to employ various other methods for collecting and analyzing pharmacokinetic, pharmacodynamic and other clinical data.

A therapeutic protein of the present methods may be an incretin mimetic. An incretin mimetic can be selected from the group of: incretin hormone and/or fragment, variant and/or conjugate thereof and GLP-1 agonist and/or fragment, variant and/or conjugate thereof. Incretin mimetics may comprise at least one fragment and/or variant of human GLP-1 conjugated with a fusion partner. Fragments and variants of GLP-1 may comprise GLP-1(7-36(A8G)), wherein alanine 8 of wild type GLP-1, such alanine being mutated to a glycine (hereinafter designated as "A8G") (See for example, the mutants disclosed in U.S. Pat. No. 5,545,618, herein incorporated by reference in its entirety). Fragments and variants of GLP-1 may be genetically fused to human serum albumin. Fragments and variants of GLP-1 may comprise at least two GLP-1(7-36(A8G)) tandemly and genetically fused to the human serum albumin. GLP-1(7-36(A8G)) may be genetically fused at the N-terminus of the human serum albumin. Therapeutic proteins of the present invention may comprise SEQ ID No.: 1.

Variants of GLP-1(7-37) may be denoted for example as Glu$^{22}$-GLP-1(7-37)OH which designates a GLP-1 variant in which the glycine normally found at position 22 of GLP-1(7-37)OH has been replaced with glutamic acid; Val$^8$-Glu$^{22}$-GLP-1(7-37)OH designates a GLP-1 compound in which alanine normally found at position 8 and glycine normally found at position 22 of GLP-1(7-37)OH have been replaced with valine and glutamic acid, respectively. Examples of variants of GLP-1 include, but are not limited to, those presented below:

-continued

| | | |
|---|---|---|
| Gly$^8$-Lys$^{22}$-GLP-1(7-37)OH | Gly$^8$-Cys$^{22}$-GLP-1(7-37)OH | Glu$^{22}$-GLP-1(7-36)OH |
| Asp$^{22}$-GLP-1(7-36)OH | Arg$^{22}$-GLP-1(7-36)OH | Lys$^{22}$-GLP-1(7-36)OH |
| Cys$^{22}$-GLP-1(7-36)OH | Val$^8$-Glu$^{22}$-GLP-1(7-36)OH | Val$^8$-Asp$^{22}$-GLP-1(7-36)OH |
| Val$^8$-Arg$^{22}$-GLP-1(7-36)OH | Val$^8$-Lys$^{22}$-GLP-1(7-36)OH | Val$^8$-Cys$^{22}$-GLP-1(7-36)OH |
| Gly$^8$-Glu$^{22}$-GLP-1(7-36)OH | Gly$^8$-Asp$^{22}$-GLP-1(7-36)OH | Gly$^8$-Arg$^{22}$-GLP-1(7-36)OH |
| Gly$^8$-Lys$^{22}$-GLP-1(7-36)OH | Gly$^8$-Cys$^{22}$-GLP-1(7-36)OH | Lys$^{23}$-GLP-1(7-37)OH |
| Val$^8$-Lys$^{23}$-GLP-1(7-37)OH | Gly$^8$-Lys$^{23}$-GLP-1(7-37)OH | His$^{24}$-GLP-1(7-37)OH |
| Val$^8$-His$^{24}$-GLP-1(7-37)OH | Gly$^8$-His$^{24}$-GLP-1(7-37)OH | Lys$^{24}$-GLP-1(7-37)OH |
| Val$^8$-Lys$^{24}$-GLP-1(7-37)OH | Gly$^8$-Lys$^{23}$-GLP-1(7-37)OH | Glu$^{30}$-GLP-1(7-37)OH |
| Val$^8$-Glu$^{30}$-GLP-1(7-37)OH | Gly$^8$-Glu$^{30}$-GLP-1(7-37)OH | Asp$^{30}$-GLP-1(7-37)OH |
| Val$^8$-Asp$^{30}$-GLP-1(7-37)OH | Gly$^8$-Asp$^{30}$-GLP-1(7-37)OH | Gln$^{30}$-GLP-1(7-37)OH |
| Val$^8$-Gln$^{30}$-GLP-1(7-37)OH | Gly$^8$-Gln$^{30}$-GLP-1(7-37)OH | Tyr$^{30}$-GLP-1(7-37)OH |
| Val$^8$-Tyr$^{30}$-GLP-1(7-37)OH | Gly$^8$-Tyr$^{30}$-GLP-1(7-37)OH | Ser$^{30}$-GLP-1(7-37)OH |
| Val$^8$-Ser$^{30}$-GLP-1(7-37)OH | Gly$^8$-Ser$^{30}$-GLP-1(7-37)OH | His$^{30}$-GLP-1(7-37)OH |
| Val$^8$-His$^{30}$-GLP-1(7-37)OH | Gly$^8$-His$^{30}$-GLP-1(7-37)OH | Glu$^{34}$-GLP-1(7-37)OH |
| Val$^8$-Glu$^{34}$-GLP-1(7-37)OH | Gly$^8$-Glu$^{34}$-GLP-1(7-37)OH | Ala$^{34}$-GLP-1(7-37)OH |
| Val$^8$-Ala$^{34}$-GLP-1(7-37)OH | Gly$^8$-Ala$^{34}$-GLP-1(7-37)OH | Gly$^{34}$-GLP-1(7-37)OH |
| Val$^8$-Gly$^{34}$-GLP-1(7-37)OH | Gly$^8$-Gly$^{34}$-GLP-1(7-37)OH | Ala$^{35}$-GLP-1(7-37)OH |
| Val$^8$-Ala$^{35}$-GLP-1(7-37)OH | Gly$^8$-Ala$^{35}$-GLP-1(7-37)OH | Lys$^{35}$-GLP-1(7-37)OH |
| Val$^8$-Lys$^{35}$-GLP-1(7-37)OH | Gly$^8$-Lys$^{35}$-GLP-1(7-37)OH | His$^{35}$-GLP-1(7-37)OH |
| Val$^8$-His$^{35}$-GLP-1(7-37)OH | Gly$^8$-His$^{35}$-GLP-1(7-37)OH | Pro$^{35}$-GLP-1(7-37)OH |
| Val$^8$-Pro$^{35}$-GLP-1(7-37)OH | Gly$^8$-Pro$^{35}$-GLP-1(7-37)OH | Glu$^{35}$-GLP-1(7-37)OH |
| Gly$^8$-Glu$^{35}$-GLP-1(7-37)OH | Val$^8$-Ala$^{27}$-GLP-1(7-37)OH | Val$^8$-His$^{37}$-GLP-1(7-37)OH |
| Val$^8$-Glu$^{22}$-Lys$^{23}$-GLP-1(7-37)OH | Val$^8$-Glu$^{22}$-Glu$^{23}$-GLP-1(7-37)OH | Val$^8$-Glu$^{22}$-Ala$^{27}$-GLP-1(7-37)OH |
| Val$^8$-Gly$^{34}$-Lys$^{35}$-GLP-1(7-37)OH | Val$^8$-His$^{37}$-GLP-1-(7-37)OH | Gly$^8$-His$^{37}$-GLP-1(7-37)OH |
| Val$^8$-Glu$^{22}$-Ala$^{27}$-GLP-1(7-37)OH | Gly$^8$-Glu$^{22}$-Ala$^{27}$-GLP-1(7-37)OH | Val$^8$-Lys$^{22}$-Glu$^{23}$-GLP-1(7-37)OH |
| Gly$^8$-Lys$^{22}$-Glu$^{23}$-GLP-1(7-37)OH. | Val$^8$-Glu$^{35}$-GLP-1(7-37)OH | |

Variants of GLP-1 may also include, but are not limited to, GLP-1 or GLP-1 fragments having chemical modification of one or more of its amino acid side groups. A chemical modification includes, but is not limited to, adding chemical moieties, creating new bonds, and removing chemical moieties. Modifications at amino acid side groups include, without limitation, acylation of lysine-ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Furthermore, one or more side groups, or terminal groups, may be protected by protective groups known to the ordinarily-skilled protein chemist.

GLP-1 fragments or variants may also include polypeptides in which one or more amino acids have been added to the N-terminus and/or C-terminus of GLP-1(7-37)OH of said fragment or variant. The amino acids in GLP-1 in which amino acids have been added to the N-terminus or C-terminus are denoted by the same number as the corresponding amino acid in GLP-1(7-37)OH. For example, the N-terminus amino acid of a GLP-1 compound obtained by adding two amino acids to the N-terminus of GLP-1(7-37)OH is at position 5; and the C-terminus amino acid of a GLP-1 compound obtained by adding one amino acid to the C-terminus of GLP-1(7-37)OH is at position 38. Thus, position 12 is occupied by phenylalanine and position 22 is occupied by glycine in both of these GLP-1 compounds, as in GLP-1(7-37)OH. Amino acids 1-6 of a GLP-1 with amino acids added to the N-terminus may be the same as or a conservative substitution of the amino acid at the corresponding position of GLP-1(1-37)OH. Amino acids 38-45 of a GLP-1 with amino acids added to the C-terminus may be the same as or a conservative substitution of the amino acid at the corresponding position of glucagon or exendin-4.

Fusion partners of therapeutic proteins of the present invention can comprise at least one polypeptide, variant and/or fragment thereof of a polypeptide selected from the group of: albumin, transferrin, and Fc portion of an IgG. Therapeutic proteins of the present invention can be selected from the group of: exendin 3, exendin 4, human GLP-1 and fragments, variants, and/or or conjugates thereof. Therapeutic proteins also include isolated polypeptide fragments, variants and/or conjugates thereof, monoclonal antibodies, which may be murine, human, humanized or chimeric, and fragments thereof or a domain antibodies.

Methods are also provided herein for detecting at least one endogenous protein in plasma from a mammal comprising contacting said plasma with a protease capable of digesting said at least one protein into at least one detectable fragment and detecting said at least one detectable fragment using high performance liquid chromatography and mass spectroscopy. The endogenous protein may be selected from the group of antibody, cytokine, tumor associated protein, at least one biomarker, and transmembrane protein.

Additionally, methods are provided for detecting at least one protein in plasma from a mammal comprising contacting said plasma with a protease capable of digesting said at least one protein wherein the protease is selected from the group of: Lys-C, Trypsin, Asp-N, Arg-C, Asn-C, Post-Proline cleaving enzyme, and CNbr. In some aspects, the mammal is a human.

Methods are also provided further comprising preparing a stable detectable standard peptide. The stable detectable standard peptide can be prepared in a separate container from said at least one protein. In such an embodiment, the stable detectable standard peptide may be digested in a separate container or may not need to be digested. In another embodiment, the standard detectable marker may be a synthetic peptide. The stable detectable standard peptide would then be used to quantify the amount of at least one protein in plasma using the methods described herein. In another aspect methods are provided wherein said stable detectable standard peptide is contacted with said plasma. The stable detectable standard peptide may be digested using a second protease, if necessary. This second protease can be the same protease used to prepare said at least one protein or may be a different protease. The stable detectable standard peptide can be detected from the same sample as the protein of interest. In one aspect, the stable detectable standard peptide is isotopically labeled.

In another aspect, methods are provided further comprising generating a peptide library of said protein. Additional methods comprise selecting a fragment of said at least one protein that will be produced upon digesting with said protease. The fragment can be separated from all other fragments of said therapeutic protein produced by said protease based on one or more of the following characteristics: charge, size, secondary structure, and tertiary structure.

In yet another aspect, high throughput methods are provided for detecting at least one endogenous protein in plasma from a mammal. In another aspect, the methods are quantitative.

The methods of the present invention may be combined with several other technologies for rapid detection of at least one protein in plasma. For instance, the methods of the present invention can be combined with microarray technology and/or nanotechnology, including microfluidic analysis systems for detection and quantification of samples using mass spectroscopy. An example of a nanoliter microfluidic analysis system is described in Andersson, et al., *Anal. Chem.* 79:4022-4030 (2007).

The following examples illustrate various aspects of this invention. These examples do not limit the scope of this invention which is defined by the appended claims.

EXAMPLES

Example 1

SEQ ID NO.:1 in Human Plasma

The following parameters were assessed:
Selectivity, sensitivity and linearity
Bias and precision
Stability of SEQ ID NO.:1 in human plasma at room temperature
The effect of freeze-thaw on the stability of SEQ ID NO.:1 in human plasma
Stability of SEQ ID NO.:1 in processed samples
The ability to dilute samples above the higher limit of quantification (HLQ)
Validation Procedure SEQ ID NO.:1 is a 73,012 Dalton (645 amino acid) genetic fusion protein consisting of two modified 30 amino acid GLP-1 peptides linked in tandem to recombinant human serum albumin. This example describes HPLC-MS/MS methods for the determination of SEQ ID NO.:1 in human plasma. 200 µL human plasma sample from a human administered SEQ ID NO.:1 was combined with an isotopically labeled GLP-1 internal standard, [$^{15}$N $^{13}$C$_6$]-GLP1M (SEQ ID NO.:3) (FIG. 3), and digested using the endoproteinase enzyme Lys-C.

Two GLP-1 specific peptide fragments (1005 and 1012Da) both from SEQ ID NO.:1 and [$^{15}$N $^{13}$C$_6$]-GLP1M were extracted from 200 µL of human plasma by solid phase extraction. Extracts were analyzed by HPLC-MS/MS using a TurboIonSpray™ interface and multiple reaction monitoring.
Sample Preparation Human plasma was transferred into 1.2 mL polypropylene 96-well tubes (Micronic Systems, Lelystad, Holland). [$^{15}$N $^{13}$C$_6$]-GLP1M was then added to each plasma sample. The plasma was enzymatically digested using endoproteinase lys-C to produce specific peptide fragments for both SEQ ID NO.:1 and [$^{15}$N $^{13}$C$_6$]-GLP1M (See FIGS. 3 and 2). The digestion was halted by adding acidified water. The prepared samples were loaded onto a mixed mode strong cat-ion exchange plate, washed, eluted, and evaporated under nitrogen before reconstituting and injection onto HPLC-MS/MS system for analysis. MS/MS detection was performed on an API4000 (Applied Biosystems/MDS Sciex) triple quadrupole instrument with thermally assisted electrospray ionization (TurboIonSpray™) and multiple reaction monitoring.

The following steps were used to prepare sample:
200 µL of plasma from a human patient, standard or QC were aliquoted into the polypropylene 96-well tubes;
50 uL of isotopically labeled GLP-1 internal standard ([$^{15}$N $^{13}$C$_6$]-GLP1M) was added to all plasma samples
50 uL of DI water were added to double blank samples
100 µL of endoproteinase lys-C (60 mIU) were added to all plasma samples and incubated at ambient room temperature for 24 hours;
300 µL of 0.1 N HCL in Milli-Q water was added to all plasma samples;
500 µL of methanol was added to a Strata X-C 10 mg/well (Phenomenex) SPE 96 well extraction plate followed by 500 µL 0.01N HCl for conditioning;
Prepared samples were loaded onto the plate and allowed to sit for approximately five minutes before applying vacuum;
500 µL 0.01N HCl followed by 500 µL methanol was added to the plate for washing;
500 µL 5% NH$_4$OH in methanol was added to the plate to elute samples;
Each sample was evaporated under nitrogen at 50° C. to dryness;
200 µL 0.1% Formic Acid/Acetonitrile (70/30, v/v) was added to reconstitute each sample; and
Each reconstituted sample was injected directly onto HPLC-MS/MS system for analysis.
Reagents for Sample preparation are described in Table 1 below:

TABLE 1

Reagents for Sample Preparation

| Reagent | Function | Preparation |
|---|---|---|
| [$^{15}$N$^{13}$C$_6$]-GLP1M | Internal Standard | H-His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-[$^{15}$N$^{13}$C$_6$]Leu-Val-Lys-Gly-Arg-OH (SEQ ID NO.: 3) Bachem, King of Prussia, PA |
| Lys C | Digestion Reagent | Endoproteinase Lys-C from *Lysobacter enzymogenes*, 3IU Sigma, St. Louis, MO |
| Lys C Solution | Digestion Reagent | Add 5 mL 100 mM Bicarbonate Buffer, pH 8.5 to 3IU Lys C. Prepare fresh daily |
| 100 mM Sodium Bicarbonate Buffer, pH 8.5 | Digestion Buffer | Add 8.401 g of sodium bicarbonate to 1 L DI water. Adjust pH to 8.5 using NaOH. Filter buffer using 0.2 micron filter. |
| Water containing 0.1% (v/v) formic acid | Mobile Phase A | Add 1 mL of formic acid to water and make up to 1000 mL with water. |
| 5% NH$_4$OH in MeOH | Elution Solution | Add 50 mL NH$_4$OH to 950 mL MeOH |
| 70:30 0.1% Formic Acid:Acetonitrile (v/v) | Reconstitution Solution | Add 70 mL of 0.1% Formic acid to 30 mL acetonitrile. |
| 40:40:20 Acetonitrile:Isopropanol:0.1% Formic acid in water | Injector and syringe Solvent Wash | Add 40 mL Acetonitrile to 40 mL Isopropanol, and 20 mL 0.1% Formic acid in water |
| 75:25 0.1% Formic acid in water:Acetonitrile | Injector and syringe Solvent Wash | Add 75 mL 0.1% Formic acid in water to 25 mL Acetonitrile |

Unless specified, all chemicals and solvents are at least AR and HPLC grade, respectively.

High Performance Liquid Chromatography

HPLC-MS/MS data were acquired and processed (integrated) using the proprietary software application Analyst (Version 1.4.1, Applied Biosystems/MDS Sciex, Canada). Calibration plots of analyte/internal standard peak area ratio versus SEQ ID NO.:1 concentration were constructed and a weighted ($1/x^2$) linear regression (sigma (m*x+c−y)^2) applied to the data. Concentrations of SEQ ID NO.:1 in validation samples were determined from the constructed calibration line, and used to calculate the bias and precision of the method.

HPLC conditions are described in Table 2 and MS/MS conditions are described in Table 3.

TABLE 2

HPLC Conditions

| HPLC conditions Autosampler | CTC HTS PAL |
|---|---|
| Injector Wash Solvent 1 | 40:40:20 Acetonitrile:Isopropanol:0.1% Formic acid in water; 2 washes |
| Injector Wash Solvent 2 | 75:25 0.1% Formic Acid in water:Acetonitrile; 2 washes |
| Syringe Wash Solvent 1 | 40:40:20 Acetonitrile:Isopropanol:0.1% Formic acid in water; 1 wash |
| Syringe Wash Solvent 2 | 75:25 0.1% Formic Acid in water:Acetonitrile; 1 wash |
| Typical Injection Volume | 5 µL, loop injection |
| Chromatography System | Flux Instruments Rheos 2000 HPLC |
| Flow Rate | 350 µL/min |
| Analytical Column | Waters Atlantis dC18 2.1 × 50 mm, 3 µm |
| Column Temperature | 30° C. |
| Run Time/Data Acquisition Time | 3.0 minutes |
| Autosampler Blocking Time | 30 seconds |
| Mobile Phase B | ACN |
| Mobile Phase D | 0.1% (v/v) formic acid in water |

TABLE 2-continued

HPLC Conditions

| | Time (min) | % B | % D |
|---|---|---|---|
| Gradient Composition | 0.0 | 15 | 85 |
| | 0.15 | 15 | 85 |
| | 1.1 | 75 | 25 |
| | 2.0 | 75 | 25 |
| | 2.1 | 15 | 85 |

Alternative, equivalent HPLC equipment may be used as appropriate. Minor changes to chromatographic conditions may be made

TABLE 3

MS/MS Conditions

| Mass Spectrometer | Applied Biosystems/MDS Sciex API-4000 |
|---|---|
| Ionisation Interface and Temperature | TurboIonSpray ® at 750° C. |
| Pause Time | 5 msec |
| Gas 1 Setting (Zero Air) | 60 psi |
| Gas 2 Setting (Zero Air) | 60 psi |
| Curtain Gas Setting (Nitrogen) | 30 |
| Collision Gas Setting (Nitrogen) | 8 |

Analytical method parameters are typical but may vary from instrument to instrument in order to achieve an equivalent response Test Compounds and Biological Matrix The amino acid sequence of SEQ ID NO.:1 is presented in FIG. 1 and its GLP-1 specific peptide fragment (SEQ ID NO.:2) is presented in FIG. 3. The amino acid sequence of isotopically labeled GLP-1 internal standard [$^{15}$N $^{13}$C$_6$]-GLP1M (SEQ ID NO.:3) and its GLP-1 specific peptide fragment (SEQ ID NO.:4) is presented in FIG. 2. Sufficient volumes of both pooled control human plasma (EDTA) for the preparation of validation samples and control human plasma from 6 individual volunteers to establish the selectivity of the method were obtained from Bioreclamation Inc. (Hicksville, N.Y.) and stored frozen at −80° C.

Preparation of Calibration Standards and Validation Samples

Validation samples to establish the bias and precision of the method were prepared from an independent set of analytical standard solutions to give nominal concentrations of SEQ ID NO.:1 in human plasma at 50, 200, 2000, 40000 and 50000 ng/mL according to the dilution schedule specified in Table 4.

TABLE 4

Calibration standards are prepared fresh as follows and thoroughly mixed.

| Standard Concentration (ng/mL) | Volume of Working Solution (μL) | | | | Total Volume in Human (EDTA) Plasma (μL) |
|---|---|---|---|---|---|
| | A4 1 μg/mL | A3 10 μg/mL | A2 100 μg/mL | A1 1000 μg/mL | |
| 50 | 50 | — | — | — | 1000 |
| 100 | 100 | — | — | — | 1000 |
| 250 | — | 25 | — | — | 1000 |
| 500 | — | 50 | — | — | 1000 |
| 1000 | — | 100 | — | — | 1000 |
| 2500 | — | — | 25 | — | 1000 |
| 5000 | — | — | 50 | — | 1000 |
| 10000 | — | — | 100 | — | 1000 |
| 25000 | — | — | — | 25 | 1000 |
| 50000 | — | — | — | 50 | 1000 |

The total volumes prepared may be scaled up or down as required

In addition to blanks and a duplicate set of calibration standards, 6 replicates at each validation sample concentration were analyzed on 3 separate occasions by the HPLC-MS/MS method. The lyophilized powder of [$^{15}$N $^{13}$C$_6$]-GLP1M was reconstituted in the appropriate amount of water to give a 1.0 mg/mL stock solution.

Quality Control/Validation Sample Preparation

Quality controls (QC) and validation samples (VS) were prepared according to the dilutions of Table 5 and thoroughly mixed. Replicate 1.4 mL aliquots were transferred to appropriate assay tubes for storage at −80° C.

TABLE 5

Quality Control and Validation Samples

| QC/VS Concentration (ng/mL) | Volume of Spiking Solution (μL) | | | | Total Volume in Human (EDTA) Plasma (μL) |
|---|---|---|---|---|---|
| | B4 1 μg/mL | B3 10 μg/mL | B2 100 μg/mL | B1 1000 μg/mL | |
| 50 [1] | 500 | — | — | — | 10 |
| 200 | — | 200 | — | — | 10 |
| 2000 | — | — | 200 | — | 10 |
| 40000 | — | — | — | 400 | 10 |
| 50000 [1] | — | — | — | 500 | 10 |
| 250000 [1] | — | — | — | 500 | 2 |

[1] Prepared for validation only
The total volumes prepared may be scaled up or down as required Digestion Procedure:

Samples were subject to digestion according to the following steps:
  Aliquot 200 μL of sample, standard or QC into Micronic tube;
  Add 50 uL of I.S. (5000 ng/mL) and vortex mix.
  Add 100 μL of Lys C Solution in 100 mM Sodium Bicarbonate buffer, pH 8.5 to all tubes; and
  Cap all tubes, vortex for 2 min., Centrifuge for 5 min. and place on shaker for 24 hours at room temperature.

Regression Model:
  Peak area ratios with 1/x$^2$ weighted linear regression.

Selection of the SEQ ID NO.:1 Fragment

SEQ ID NO.: 2, a 1005 Da fragment of SEQ ID NO.:1, was selected for monitoring based on the analysis of the peptide map generated using the endoproteinase enzyme Lys-C. This fragment contains the amino acid sequence that is specific for the GLP-1 moiety of the fusion protein and there are no other similar amino acid sequences contained within this protein that can be formed when digested with Lys-C. Since two tandem copies of GLP-1 are linked to one molecule of human serum albumin SEQ ID NO.:2 is released from SEQ ID NO.:1 at a molar ratio of 2/1. The selectivity of the 1005 fragment in human plasma was confirmed during the selectivity phase of the validation as described below.

Selectivity, Sensitivity and Linearity

The precursor ion at m/z 503 is the [M+2H]$^{2+}$ ion of the GLP-1 parent ion fragment. The characteristic precursor [M+2H]$^{2+}$ to product ions transitions, m/z 503 to 616 and [M+H]$^{1+}$ 507 to 623 are consistent with the structures of SEQ ID NO.:1 and the internal standard, respectively, and are used as multiple reaction monitoring transitions to ensure high selectivity. The selectivity of the method was established by the analysis of samples of control human plasma from 6 individual volunteers. The selectivity of the method was also assessed by the inclusion of blank and double blank samples prepared from pooled control human plasma in validation assays. HPLC-MS/MS chromatograms of the blanks and validation samples were visually examined and compared for chromatographic integrity and potential interferences. No unacceptable interferences at the retention times of SEQ ID NO.:1 and its internal standard SEQ ID NOs.:2 and 3 were observed.

Linear responses in the analyte/internal standard peak area ratios were observed over the range 50 to 50000 ng/mL. The correlation coefficients obtained using 1/x$^2$ weighted linear regression were better than 0.9964.

Bias and Precision

Concentrations of SEQ ID NO.:1 in validation samples were determined from the calibration line on each occasion and are presented in Table 6 along with accuracy and precision values. At all validation sample concentrations examined, the bias was less than 15%, and is therefore acceptable. The maximum bias observed was −12.8%. At all validation sample concentrations examined, the within- and between-run precision values were less than or equal to 15%, and are therefore acceptable. The maximum within- and between-run precision values observed were 4.3% and 8.6%, respectively. As defined by the lower and upper validation sample concentrations possessing acceptable accuracy and precision, the validated range of this method for SEQ ID NO.:1 based on 200 μL of human plasma is 50 to 50000 ng/mL. Bias, precision and individual sample concentrations for SEQ ID NO.:1 in human plasma are presented in Table 6.

TABLE 6

Bias, Precision and Individual Validation Sample Concentrations for SEQ ID NO.: 1 in Human Plasma

| | Nominal Concentrations (ng/mL) | | | | |
|---|---|---|---|---|---|
| | 50000.0 | 40000.0 | 2000.0 | 200.0 | 50.0 |
| RUN 1 | 42484.2 | 36745.2 | 1973.5 | 190.2 | 52.0 |
| | 43269.5 | 34922.2 | 1858.4 | 191.7 | 53.8 |
| | 43978.6 | 35295.2 | 1939.2 | 198.3 | 51.9 |
| | 44625.2 | 37083.3 | 2051.7 | 191.7 | 48.1 |
| | 45750.7 | 37995.6 | 2019.3 | 185.7 | 52.4 |
| | 45348.3 | 37548.6 | 2022.9 | 191.1 | 49.5 |

TABLE 6-continued

Bias, Precision and Individual Validation Sample
Concentrations for SEQ ID NO.: 1 in Human Plasma

| | Nominal Concentrations (ng/mL) | | | | |
|---|---|---|---|---|---|
| | 50000.0 | 40000.0 | 2000.0 | 200.0 | 50.0 |
| Mean (ng/mL) | 44242.7 | 36598.4 | 1977.5 | 191.4 | 51.3 |
| S.D. | 1245.2 | 1234.5 | 70.7 | 4.0 | 2.1 |
| Precision (% CV) | 2.8 | 3.4 | 3.6 | 2.1 | 4.1 |
| Bias % | −11.5 | −8.5 | −1.1 | −4.3 | 2.5 |
| RUN 2 | 44794.1 | 36115.3 | 1969.9 | 183.9 | 49.9 |
| | 45633.8 | 36255.7 | 1942.6 | 193.7 | 49.2 |
| | 47046.1 | 36546.3 | 1905.1 | 191.0 | 51.6 |
| | 45970.4 | 38586.5 | 1993.3 | 194.8 | 47.7 |
| | 47692.8 | 38139.1 | 2017.4 | 192.9 | 53.7 |
| | 47105.3 | 38066.7 | 1936.7 | 194.2 | 51.8 |
| Mean (ng/mL) | 46373.7 | 37284.9 | 1960.8 | 191.8 | 50.6 |
| S.D. | 1089.3 | 1096.1 | 40.9 | 4.1 | 2.2 |
| Precision (% CV) | 2.3 | 2.9 | 2.1 | 2.1 | 4.3 |
| Bias % | −7.3 | −6.8 | −2.0 | −4.1 | 1.3 |
| RUN 3 | 44778.2 | 36456.2 | 1932.0 | 205.2 | 47.0 |
| | 46028.4 | 37233.5 | 1976.7 | 200.9 | 43.8 |
| | 43876.0 | 37764.2 | 2004.3 | 193.5 | 42.9 |
| | 48575.9 | 38645.0 | 1895.1 | 199.8 | 43.5 |
| | 46740.1 | 37869.4 | 2073.3 | 191.1 | 41.9 |
| | 48170.0 | 39850.3 | 2051.7 | 194.8 | 42.6 |
| Mean (ng/mL) | 46361.4 | 37969.8 | 1988.9 | 197.5 | 43.6 |
| S.D. | 1850.0 | 1172.8 | 68.5 | 5.3 | 1.8 |
| Precision (% CV) | 4.0 | 3.1 | 3.4 | 2.7 | 4.1 |
| Bias % | −7.3 | −5.1 | −0.6 | −1.2 | −12.8 |
| Overall Statistics | | | | | |
| Mean (ng/mL) | 45659.3 | 37284.4 | 1975.7 | 193.6 | 48.5 |
| S.D. | 1695.3 | 1240.2 | 59.0 | 5.1 | 4.0 |
| Precision (%) | 3.7 | 3.3 | 3.0 | 2.6 | 8.3 |
| Bias (%) | −8.7 | −6.8 | −1.2 | −3.2 | −3.0 |
| Average Within-run precision (%) | 3.1 | 3.1 | 3.1 | 2.3 | 4.2 |
| Between-run precision (%) | 2.4 | 1.3 | Negligible | 1.5 | 8.6 |

The ability to dilute samples containing SEQ ID NO.:1 at concentrations above the HLQ was demonstrated by performing 6 replicate 10-fold dilutions of human plasma samples spiked at 250000 ng/mL. Concentrations of SEQ ID NO.:1 in these matrix dilution samples were determined and corrected for the dilution factor. The bias and within-run precision values are less than 15% (actually −3.4% and 4.5%, respectively) indicating that a 10-fold dilution of human plasma samples containing SEQ ID NO.:1 above the HLQ is valid.

Conclusion

This method was successfully validated over the range of 50.0-50000 ng/mL for SEQ ID NO.:1 in human plasma and proved to be highly selective, precise, and accurate. The use of specific proteolytic digestion followed by solid-phase extraction and quantitative tandem mass spectrometry proved to be a very successful approach, offering a substantial increase in robustness over conventional immunochemical methods. Based on this method, clinical SEQ ID NO.:1 samples can be processed in approximately the same period of time as many small molecule quantitative tandem mass spectrometry methods.

Example 2

An additional assessment of method performance was determined by comparing the results obtained from human clinical study samples with results obtained using sandwich ELISA technique.

In the validated ELISA procedure, clinical samples were diluted 100-fold with sample buffer prior to analysis. The fusion protein was captured using a rabbit anti-human GLP-1 (7-36) amide and detected using a rabbit anti-HSA conjugated to biotin. Streptavidin HRP conjugate was used as the detection enzyme in conjunction with a chemiluminescent substrate. Sample concentrations were determined by interpolation from the standard curve, which was fitted using a weighted (1/x). four parameter logistic equation. The validated range of this assay, based on 10 uL of human plasma is 50 to 15000 ng/mL.

A method correlation plot for data generated using high performance liquid chromatography and mass spectroscopy methods of Example 1 and the ELISA method of this example was generated using sample results obtained from 612 clinical samples. The method correlation plot is presented in FIG. 4. The linear regression analysis yielded a correlation coefficient (r) of 0.9692, with an intercept at −83.4 ng/mL ($p<0.001$), and a slope of 0.725 ($p<0.001$) between the methods. The statistical results from the linear regression analysis indicate that the intercept and the slope are significantly different from 0 ($p<0.001$) and 1 ($p<0.001$); however, the negative slope bias observed is well within the range of the combined method accuracies. It should be noted that although differences in sample concentration results exist between the two methods, the overall pattern of the clinical PK data remains the same.

Example 3

Incurred sample reanalysis of clinical samples was performed in order to confirm both assay robustness and reproducibility. Clinical samples from both healthy and type 2 diabetic patients were reanalyzed on three separate occasions. Incurred sample reproducibility is confirmed when the difference between run CV for the three runs is ≤15%. Results from the incurred sample reanalysis test are presented in Table 7. Incurred sample reproducibility was confirmed in both healthy and type 2 diabetic patients.

TABLE 7

Incurred Sample Reproducibility

| | Run 1 ng/mL | Run 2 ng/mL | Run 3 ng/mL |
|---|---|---|---|
| Healthy | 3912.5 | 3669.2 | 3701.8 |
| | 3946.5 | 3868.8 | 3953.6 |
| | 3973.9 | 3826.6 | 4087.6 |
| Mean | 3944.3 | 3788.2 | 3914.3 |
| % CV | 0.8 | 2.8 | 5.0 |
| Mean (Between run) | | 3882.3 | |
| % CV (Between run) | | 2.1 | |
| T2DM | 304.9 | 301.6 | 302.6 |
| | 319.8 | 316.6 | 317.3 |
| | 332.1 | 307.6 | 327.3 |
| Mean | 318.9 | 308.6 | 315.7 |
| % CV | 4.3 | 2.4 | 3.9 |
| Mean (Between run) | | 314.4 | |
| % CV (Between run) | | 1.7 | |

The invention claimed is:

1. A method for detecting at least one therapeutic protein in plasma from a mammal comprising contacting said plasma with a first protease capable of digesting said at least one therapeutic protein into at least one detectable fragment and detecting said at least one detectable fragment using high performance liquid chromatography and mass spectroscopy, wherein said at least one therapeutic protein comprises at least two GLP-1(7-36(A8G)) tandemly and genetically fused to human serum albumin.

2. The method of claim 1, wherein the at least two GLP-1 (7-36(A8G)) are genetically fused at the N-terminus of the human serum albumin.

3. The method of claim 1, wherein said therapeutic protein comprises SEQ ID NO:1.

4. The method of claim 1, wherein said first protease is selected from the group of: Lys-C, Trypsin, Asp-N, Arg-C, Asn-C, and Post-Proline cleaving enzyme.

5. The method of claim 1, wherein said mammal is a human.

6. The method of claim 1, further comprising preparing a stable detectable standard peptide.

7. The method of claim 6, wherein said stable detectable standard peptide is prepared in a separate container from said at least one therapeutic protein.

8. The method of claim 6, wherein said stable detectable standard peptide is contacted with said plasma.

9. The method of claim 8, wherein said stable detectable standard peptide is further digested with a second protease.

10. The method of claim 9, wherein said second protease is selected from the group of: Lys-C, Trypsin, Asp-N, Arg-C, Asn-C, and Post-Proline cleaving enzyme.

11. The method of claim 10, wherein said first and second protease are the same.

12. The method of claim 6, wherein said stable detectable standard peptide is isotopically labeled.

13. The method of claim 1, further comprising generating a peptide library of said therapeutic protein.

14. The method of claim 13, further comprising selecting a fragment of said at least one protein that will be produced upon digesting with said protease.

15. The method of claim 14, wherein said fragment can be separated from all other fragments of said therapeutic protein produced by said protease based on one or more of the following characteristics: mass, charge, size, secondary structure, and tertiary structure.

16. The method of claim 1, wherein said method is a high throughput method.

17. The method of claim 1, wherein said method is quantitative.

18. The method of claim 1, further comprising calculating at least one pharmacokinetic parameter of said at least one therapeutic protein in plasma.

19. The method of claim 1, further comprising calculating at least one pharmacodynamic parameter of said at least one therapeutic protein in plasma.

20. The method of claim 1, wherein sample reproducibility is confirmed by ELISA.

* * * * *

SEQUENCE LISTING

<160> NUMBER OF SEQ ID NOS: 3

<210> SEQ ID NO 1
<211> LENGTH: 645
<212> TYPE: PRT
<213> ORGANISM: homo sapiens

<400> SEQUENCE: 1

```
His Gly Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg His Gly
             20                  25                  30

Glu Gly Thr Phe Thr Ser Asp Val Ser Ser Tyr Leu Glu Gly Gln Ala
         35                  40                  45

Ala Lys Glu Phe Ile Ala Trp Leu Val Lys Gly Arg Asp Ala His Lys
     50                  55                  60

Ser Glu Val Ala His Arg Phe Lys Asp Leu Gly Glu Glu Asn Phe Lys
 65                  70                  75                  80

Ala Leu Val Leu Ile Ala Phe Ala Gln Tyr Leu Gln Gln Cys Pro Phe
                 85                  90                  95

Glu Asp His Val Lys Leu Val Asn Glu Val Thr Glu Phe Ala Lys Thr
            100                 105                 110

Cys Val Ala Asp Glu Ser Ala Glu Asn Cys Asp Lys Ser Leu His Thr
        115                 120                 125

Leu Phe Gly Asp Lys Leu Cys Thr Val Ala Thr Leu Arg Glu Thr Tyr
    130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
            180                 185                 190

Thr Phe Leu Lys Lys Tyr Leu Tyr Glu Ile Ala Arg Arg His Pro Tyr
        195                 200                 205

Phe Tyr Ala Pro Glu Leu Leu Phe Phe Ala Lys Arg Tyr Lys Ala Ala
    210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                245                 250                 255

Arg Leu Lys Cys Ala Ser Leu Gln Lys Phe Gly Glu Arg Ala Phe Lys
            260                 265                 270

Ala Trp Ala Val Ala Arg Leu Ser Gln Arg Phe Pro Lys Ala Glu Phe
        275                 280                 285

Ala Glu Val Ser Lys Leu Val Thr Asp Leu Thr Lys Val His Thr Glu
    290                 295                 300

Cys Cys His Gly Asp Leu Leu Glu Cys Ala Asp Asp Arg Ala Asp Leu
305                 310                 315                 320

Ala Lys Tyr Ile Cys Glu Asn Gln Asp Ser Ile Ser Ser Lys Leu Lys
                325                 330                 335

Glu Cys Cys Glu Lys Pro Leu Leu Glu Lys Ser His Cys Ile Ala Glu
            340                 345                 350

Val Glu Asn Asp Glu Met Pro Ala Asp Leu Pro Ser Leu Ala Ala Asp
        355                 360                 365
```

```
Phe Val Glu Ser Lys Asp Val Cys Lys Asn Tyr Ala Glu Ala Lys Asp
        370                 375                 380
Val Phe Leu Gly Met Phe Leu Tyr Glu Tyr Ala Arg Arg His Pro Asp
385                 390                 395                 400
Tyr Ser Val Val Leu Leu Leu Arg Leu Ala Lys Thr Tyr Glu Thr Thr
                405                 410                 415
Leu Glu Lys Cys Cys Ala Ala Ala Asp Pro His Glu Cys Tyr Ala Lys
            420                 425                 430
Val Phe Asp Glu Phe Lys Pro Leu Val Glu Glu Pro Gln Asn Leu Ile
        435                 440                 445
Lys Gln Asn Cys Glu Leu Phe Glu Gln Leu Gly Glu Tyr Lys Phe Gln
450                 455                 460
Asn Ala Leu Leu Val Arg Tyr Thr Lys Val Pro Gln Val Ser Thr
465                 470                 475                 480
Pro Thr Leu Val Glu Val Ser Arg Asn Leu Gly Lys Val Gly Ser Lys
                485                 490                 495
Cys Cys Lys His Pro Glu Ala Lys Arg Met Pro Cys Ala Glu Asp Tyr
            500                 505                 510
Leu Ser Val Val Leu Asn Gln Leu Cys Val Leu His Glu Lys Thr Pro
        515                 520                 525
Val Ser Asp Arg Val Thr Lys Cys Cys Thr Glu Ser Leu Val Asn Arg
530                 535                 540
Arg Pro Cys Phe Ser Ala Leu Glu Val Asp Glu Thr Tyr Val Pro Lys
545                 550                 555                 560
Glu Phe Asn Ala Glu Thr Phe Thr Phe His Ala Asp Ile Cys Thr Leu
                565                 570                 575
Ser Glu Lys Glu Arg Gln Ile Lys Lys Gln Thr Ala Leu Val Glu Leu
            580                 585                 590
Val Lys His Lys Pro Lys Ala Thr Lys Glu Gln Leu Lys Ala Val Met
        595                 600                 605
Asp Asp Phe Ala Ala Phe Val Glu Lys Cys Cys Lys Ala Asp Asp Lys
610                 615                 620
Glu Thr Cys Phe Ala Glu Glu Gly Lys Lys Leu Val Ala Ala Ser Gln
625                 630                 635                 640
Ala Ala Leu Gly Leu
                645

<210> SEQ ID NO 2
<211> LENGTH: 8
<212> TYPE: PRT
<213> ORGANISM: Homo sapiens

<400> SEQUENCE: 2

Glu Phe Ile Ala Trp Leu Val Lys
1               5

<210> SEQ ID NO 3
<211> LENGTH: 32
<212> TYPE: PRT
<213> ORGANISM: Homo Sapiens

<400> SEQUENCE: 3

His His Gly Glu Gly Thr Phe Thr Ser Asp Val Ser Ser Tyr Leu Glu
1               5                   10                  15
Gly Gln Ala Ala Lys Glu Phe Ile Ala Trp Leu Val Lys Gly Arg His
            20                  25                  30
```